(12) United States Patent
Chu et al.

(10) Patent No.: US 9,616,167 B2
(45) Date of Patent: Apr. 11, 2017

(54) ANESTHETIC DELIVERY DEVICE

(75) Inventors: Michael S. H. Chu, Brookline, MA (US); Peter J. Pereira, Mendon, MA (US); Jozef Slanda, Milford, MA (US); Kenneth M. Flynn, Woburn, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 902 days.

(21) Appl. No.: 13/474,470

(22) Filed: May 17, 2012

(65) Prior Publication Data
US 2012/0302993 A1   Nov. 29, 2012

Related U.S. Application Data

(60) Provisional application No. 61/489,458, filed on May 24, 2011.

(51) Int. Cl.
*A61M 5/142* (2006.01)
*A61M 5/14* (2006.01)

(52) U.S. Cl.
CPC . *A61M 5/14216* (2013.01); *A61M 2005/1405* (2013.01)

(58) Field of Classification Search
CPC .......... A61M 5/14212; A61M 5/14224; A61M 5/1424; A61M 5/14586; A61M 5/148; A61M 5/152; A61M 2005/1405; A61M 3/0262; A61M 5/282; A61C 17/02; A61C 17/0202; A61C 17/0208; B05C 17/00; B05C 17/002; B05C 17/005; B05C 17/00506; B05C 17/00509; B05C 17/00513; B05C 17/00516;
(Continued)

(56) References Cited

U.S. PATENT DOCUMENTS 1,488,777 A * 4/1924 Clements ................ A61M 3/00
                                                                15/405
1,762,237 A * 6/1930 Moore ..................... A61C 17/02
                                                                604/212
(Continued)

FOREIGN PATENT DOCUMENTS

EP    0483759 A1   5/1992
WO    87/00758 A1  2/1987
(Continued)

OTHER PUBLICATIONS

International Search Report and Written Opinion for PCT Patent Application No. PCT/US2012/038770, mailed on Jul. 5, 2012, 14 pages.
(Continued)

*Primary Examiner* — Kami A Bosworth
(74) *Attorney, Agent, or Firm* — Brake Hughes Bellerman LLP

(57) ABSTRACT

According to an example embodiment, a delivery device may include a needle and a pump operatively coupled to the needle, the pump having an expanded configuration and a collapsed configuration, the pump being biased to its expanded configuration such that fluid stored in the pump will exit the pump via the needle in response to pressure being applied to the pump, and in response to the pressure being released from the pump, the pump is configured to receive fluid from outside of the delivery device via the needle.

18 Claims, 14 Drawing Sheets

(58) Field of Classification Search
CPC .......... B05C 17/0054; B05C 17/00569; B05C 17/00573; B05C 17/00583
USPC ................................................ 604/212
See application file for complete search history.

(56) References Cited

U.S. PATENT DOCUMENTS

| | | | | |
|---|---|---|---|---|
| 2,029,483 | A * | 2/1936 | Holland | A61M 3/00 |
| | | | | 604/212 |
| 4,692,151 | A * | 9/1987 | Blackman | A61M 5/155 |
| | | | | 222/212 |
| 4,904,243 | A | 2/1990 | Bruera | |
| 4,973,250 | A * | 11/1990 | Milman | A61C 19/06 |
| | | | | 433/215 |
| 5,211,632 | A * | 5/1993 | Tsukada | 604/132 |
| 5,219,334 | A * | 6/1993 | Tsukada | 604/132 |
| 5,238,026 | A * | 8/1993 | Goto | 138/30 |
| 5,713,874 | A * | 2/1998 | Ferber | A61M 5/32 |
| | | | | 604/1 |
| 6,162,202 | A * | 12/2000 | Sicurelli et al. | 604/272 |
| 6,277,100 | B1 * | 8/2001 | Raulerson | A61M 25/0693 |
| | | | | 604/167.01 |
| 6,537,260 | B1 * | 3/2003 | Lamb | A61M 31/00 |
| | | | | 604/279 |
| 2002/0077597 | A1 | 6/2002 | Hart et al. | |
| 2003/0040709 | A1 * | 2/2003 | Mason | 604/141 |
| 2006/0253087 | A1 * | 11/2006 | Vlodaver | A61F 11/00 |
| | | | | 604/275 |
| 2008/0269716 | A1 * | 10/2008 | Bonde et al. | 604/506 |
| 2009/0137861 | A1 | 5/2009 | Goldberg et al. | |
| 2009/0163866 | A1 * | 6/2009 | Hines | A61M 5/14212 |
| | | | | 604/131 |

FOREIGN PATENT DOCUMENTS

| | | |
|---|---|---|
| WO | 91/08002 A1 | 6/1991 |
| WO | 93/00944 A1 | 1/1993 |
| WO | 97/33637 A1 | 9/1997 |
| WO | 2012/162216 A1 | 11/2012 |

OTHER PUBLICATIONS

International Preliminary Report on Patentability for PCT Patent Application No. PCT/US2012/038770, mailed on Dec. 5, 2013, 8 pages.
"Pinch Clamps", qosina.com, Product Illustrations, pp. 196109-197109.
"Checkvalves", qosina.com, Product Illustrations, pp. 92/09-93/09.

* cited by examiner

ANESTHETIC DELIVERY DEVICE

CROSS-REFERENCE TO RELATED APPLICATION

This application claims priority to U.S. Provisional Patent Application No. 61/489,458, filed on May 24, 2011, entitled "ANESTHETIC DELIVERY DEVICE", the disclosure of which is hereby incorporated by reference in its entirety.

TECHNICAL FIELD

This description relates to anesthetic delivery devices and more particularly to anesthetic delivery devices that can be used to receive fluid from a body of a patient.

BACKGROUND

Delivery devices may be used to inject anesthetics into patients. The delivery devices may include a needle for penetration of the tissues of the patient, and a reservoir for storage of the anesthetics. A practitioner may insert the needle into the patient, and then inject the anesthetics from the reservoir into the patient through the needle.

Using some known delivery devices, however, a practitioner may not know whether the needle is in the correct anatomical region of the patient. For example, a practitioner or user of the known delivery devices might not know whether the tip of the needle is disposed within an organ, such as a bladder, a blood vessel, or a tissue.

Accordingly, it is desirable to provide a delivery device that allows the practitioner or user to determine the type of material that the tip of the device is disposed within.

SUMMARY

According to an example embodiment, a delivery device may include a needle and a pump operatively coupled to the needle. The pump has an expanded configuration and a collapsed configuration. The pump is biased to its expanded configuration such that fluid stored in the pump will exit the pump via the needle in response to pressure being applied to the pump. In response to the pressure being released from the pump, the pump is configured to receive fluid from outside of the delivery device via the needle.

According to another example embodiment, a delivery device may include a needle, and a pump operatively coupled to the needle. The pump is configured to store medicinal fluid for injection into a patient via the needle. The device also includes a reservoir removably coupled to the pump. The reservoir may be configured to store and provide the medicinal fluid to the pump.

According to an example embodiment, a method may include injecting a needle of a delivery device into a patient, delivering a medicinal fluid from the delivery device into the patient by applying pressure to a pump of the delivery device, and receiving a bodily fluid from the patient into the delivery device by releasing the pressure from the pump.

The details of one or more implementations are set forth in the accompanying drawings and the description below. Other features will be apparent from the description and drawings, and from the claims.

DETAILED DESCRIPTION

The devices and methods described herein are generally directed to insertion or delivery tools for placing implants within a body of a patient. The implants delivered with the insertion or delivery tools may be used in any portion of a body of a patient. In some embodiments, the implants include, but are not limited to, implants that are placed within a pelvic region of a patient. For example, the implants that may be placed with the disclosed insertion or delivery tools include posterior support implants, anterior support implants, and/or total pelvic floor repair implants. Such implants can be placed into the pelvic space of a patient and secured at any of several locations within the pelvic space to treat many different pelvic floor dysfunctions. For example, an implant can be secured to a sacrospinous ligament or a ureterosacral ligament for uterine preservation (e.g., if a prolapsed uterus is otherwise healthy, a hysterectomy is not preformed and the uterus is re-suspended with an implant), or for posterior support. In another embodiment, an implant can be secured to pubo-urethral tissue or an obturator muscle (e.g., internus or externus) and/or membrane (each also referred to herein as "obturator") to treat, for example, incontinence. In yet another embodiment, an implant can be secured to a sacrospinous ligament or an arcus tendineus fascia pelvis (i.e., white line) (also referred to herein as "arcus tendineus") for paravaginal repairs including, for example, cystoceles, rectoceles and enteroceles. An implant can also be secured to various combinations of such locations. The insertion tools, implants, and procedures described herein may be used in a female patient or a male patient.

In some embodiments, the disclosed insertion or delivery tool(s) may be used to place an implant, for example, through a vaginal incision, in a retro-pubic direction (behind the pubic bone), or in a pre-pubic direction (in front of the pubic bone). In other embodiments, an implant can be placed in the direction of other anatomical structures or tissues as desired. A procedure to deploy a pelvic implant can include vaginal incisions, such as an anterior vaginal incision and/or a posterior vaginal incision. In some embodiments, a procedure may include an exterior incision.

Figure 1:
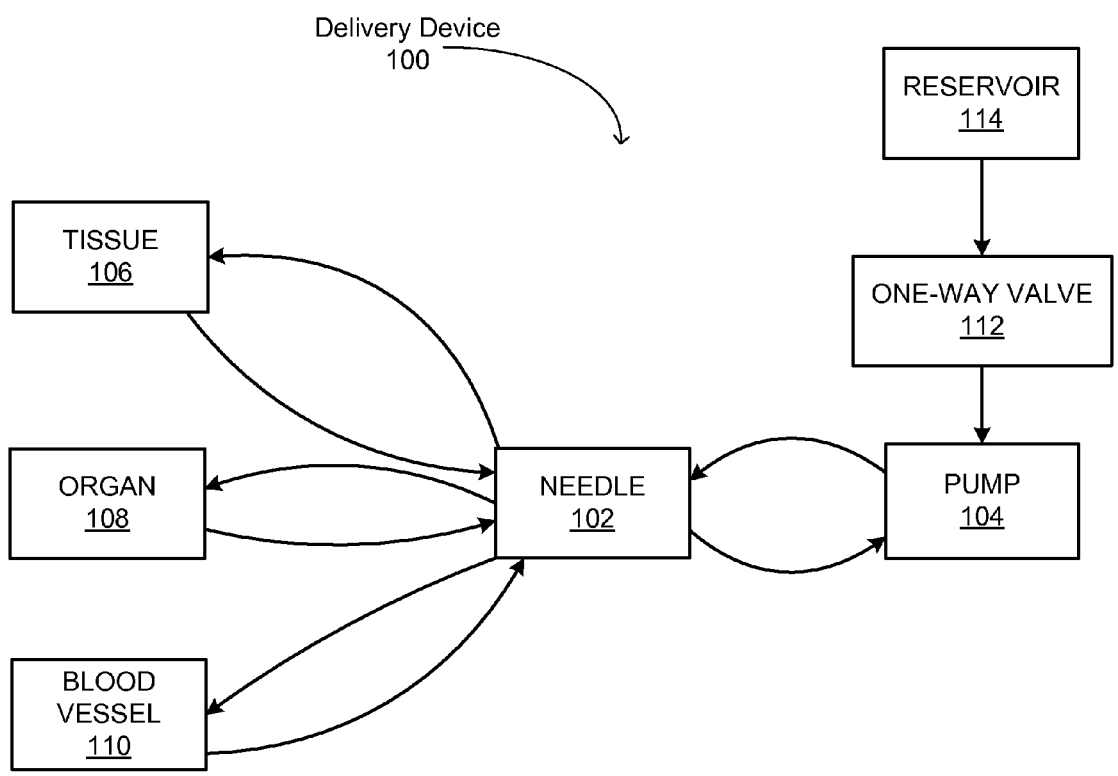
FIG. 1 is a block diagram of a delivery device according to an example embodiment.

FIG. 1 is a block diagram of a delivery device 100 according to an example embodiment. The delivery device 100 may be used to inject fluids, such as medicinal fluids, into a patient. For example, the delivery device 100 may be used to deliver anesthetic fluids to a patient. The delivery device 100 may facilitate injection of anesthetics before or during a procedure to place a medial implant for treatment of male or female incontinence within a body of a patient. The delivery device 100 may also guide the placement of an incontinence sling under the patient's urethra, while avoiding penetration of the patient's urethra or bladder. Aspiration of fluid from the patient back into the delivery device 100 may allow a user or practitioner of the delivery device 100 to determine whether a needle tip of the delivery device 100 is at an undesired location, such as the patient's urethra, bladder, or a blood vessel, by viewing a color of the aspirated fluid.

The delivery device 100 may include a needle 102. The needle 102 may be elongated and may be made of rigid material, such as metal, including stainless steel. The material may be sufficiently rigid to penetrate tissues 106, such as skin, of a patient. The needle 102 may include lumen via which the fluids, such as the anesthetic fluid, may travel through the needle 102 into the tissues of the patient. The needle 102 may be curved, allowing for the needle 102 to bypass organs 108, blood vessels 110, and bones. For example, if the delivery device 100 is used to treat stress urinary incontinence by delivering anesthetic and/or guiding a sling under a patient's urethra, the curved shape of the needle 102 may allow a practitioner to bypass the patient's pubic rambus for a transobturator approach, or bypass a pubic bone lateral to a symphysis for a retropubic approach.

In some embodiments, the needle 102 of the delivery device 100 includes a coupling mechanism for coupling the delivery device 100 to a bodily implant. In some embodiments, the needle 102 is configured to be removably coupled to an implant. For example, in some embodiments, the needle 102 includes a slot configured to receive and couple to a portion of an implant. In other embodiments, the needle 102 or another portion of the delivery device 100 includes a mechanism for removably coupling an implant. Thus, an implant can be coupled to the delivery device 100, inserted into a body of a patient, and removed from the delivery device 100 to dispose the implant within a body of a patient.

The delivery device 100 may also include a pump 104. The pump 104 may store fluids, such as the medicinal fluid or anesthetic, and also may store fluids which come back into the delivery device 100 via the needle 102. The pump 104 may be operatively coupled to the needle 102, allowing the fluids to travel from the pump 104 into the patient via the needle 102, and from the patient into the pump 104 via the needle 102. The fluid may travel to and from the patient in response to pressure being applied to and released from the pump 104, and in response to fluid being forced out of a reservoir 114, both of which mechanisms are discussed below. The pump 104 may also be rigidly connected to the needle 102. The rigid connection between the pump 104 and the needle 102 may cause movement or pressure on the pump 104 to be transferred to the needle 102, allowing a user or practitioner to control movement of the needle 102 by holding and controlling the pump 104, according to an example embodiment.

The pump 104 may be made of a transparent material, such as a plastic material. The transparent material may allow for a user of the delivery device 100 to see a color of the fluid stored in the pump 104. In example embodiments, the pump 104 may receive fluids from the patient via the needle 102 and determine what type of fluid is in the pump 104 based on the color. The type of fluid may indicate whether the needle 102 entered into a type of tissue 106 of the patient which may desirable, such as if the needle 102 has stayed below the patient's urethra, or whether the needle 102 entered an undesired organ 108. If the needle 102 enters an undesired organ 108 such as the patient's bladder, the pump 104 may receive urine via the needle 102, which may be yellow; if the needle enters a blood vessel 110 of the patient, the pump 104 may receive blood via the needle 102, which may be red. Conversely, of the needle 102 is within retracted tissue, the pump 104 may receive a clear fluid or no fluid via the needle 102. The practitioner may see the yellow or red through the transparent pump 104 and determine that the needle 102 entered the patient's bladder or blood vessel, respectively, and adjust the course of the needle 102 accordingly.

The operative coupling of the pump 104 to the needle 102 may allow the pump 104 to provide fluid to the needle 102, and for the pump 104 to receive fluid from the needle 102. The pump 104 may have an expanded configuration and a collapsed configuration, which may allow a practitioner to control whether fluid enters or exits the pump 104 via the needle by applying pressure to, and releasing pressure from, the pump 104. The collapsed configuration of the pump 104 may have a smaller volume, allowing the pump 104 to hold or store a smaller amount of fluid, than the expanded configuration. The pump 104 may be biased to its expanded configuration, returning to its expanded configuration in the absence of any pressure applied to the pump 104. The fluid stored in the pump 104 may exit the pump 104 into the patient's body via the needle 102 in response to pressure being applied to the pump 104. When the pressure is released from the pump 104, the pump 104 may return to its expanded state, causing fluid to flow back into the pump 104 from the patient via the needle 102.

The pump 104 may, for example, have a bulbous or rounded shape, and be made of a flexible material such as plastic or rubber. The bulbous or rounded shape and flexible material may bias the pump 104 to the expanded configuration, but allow the pump 104 to deform to its collapsed configuration in response to a user or practitioner applying pressure to the pump 104, and return the pump to its expanded configuration in response to the pressure being released from the pump 104. In another example, the pump 104 may include a spring or other elastic material which biases the pump 104 to the expanded configuration. For example, a spring may resist pressure forcing a barrel or other component into an aperture or cavity of the pump 104 as the pump 104 transitions into its collapsed state, and may cause the barrel or other component to move back out of the aperture or cavity as the pump 104 moves back into its expanded configuration as the pressure is released from the pump 104.

The delivery device 100 may also include a one-way valve 112. The one-way valve 112 may couple the pump 104 to a reservoir 114. In another embodiment, the one-way valve 112 is operatively coupled between the pump 104 and the reservoir 114. The one-way valve 112 may allow fluid to flow from the reservoir 114 to the pump 104, but prevent fluid from flowing from the pump 104 into the reservoir 114. The one-way valve 112 may have a cracking pressure at which the fluid begins to flow from the reservoir 114 to the pump 104 through the one-way valve 112; the cracking pressure may, for example, be about 0.112 psi. In other embodiments, the one-way valve 112 has a different cracking pressure, such as a cracking pressure of greater than 0.112 psi or a cracking pressure of less than 0.112 psi.

The one-way valve 112 may have a cracking pressure (a pressure which causes the one-way valve 112 to open) such that suction is provided to the open needle lumen first when the cracking pressure of the one-way valve 112 has not been met. When the cracking pressure is met, the one-way valve 112 may open to refill from the reservoir 114. If a tip of the needle 102 is inside tissue 106, the tissue 106 may block the needle lumen (preventing fluid from entering the needle lumen) and the suction from the pump 104 may open the one-way valve 112 to refill from the reservoir 114. Suction of fluid can occur concurrently in both the lumen of the needle 102 and from the reservoir 114, according to an example embodiment.

The reservoir 114 may store and provide the fluid, such as the medicinal fluid or anesthetic, to the pump 104. The reservoir 114 may provide the medicinal fluid, such as the anesthetic, to the pump 104 via the one-way valve 112. The reservoir 114 may be removably coupled to the pump 104, and may continue to store and fully enclose the fluid upon decoupling from the pump 104. The one-way valve 112 may allow the fluid to flow from the reservoir 114 into the pump 104, but may prevent fluid from flowing from the pump 104 into the reservoir 114. The one-way valve 112 may be coupled to the pump 104 by friction fitting, or by securement of tabs from one component into grooves of another component, or any combination thereof. For example, the one-way valve 112 may include a tabbed hub configured to screw into a threaded cylinder of the reservoir 114, and/or may include a luer hub configured to screw into a threaded cylinder of the reservoir 114.

A user or practitioner may pour or deposit the fluid into the reservoir 114, and may seal the reservoir 114, such as by inserting a plunger into a barrel of the reservoir 114 (described below). The user may prime the delivery device 100 by depressing the plunger and/or applying pressure to the pump 104 to remove air from the delivery device 100.

Figure 2:
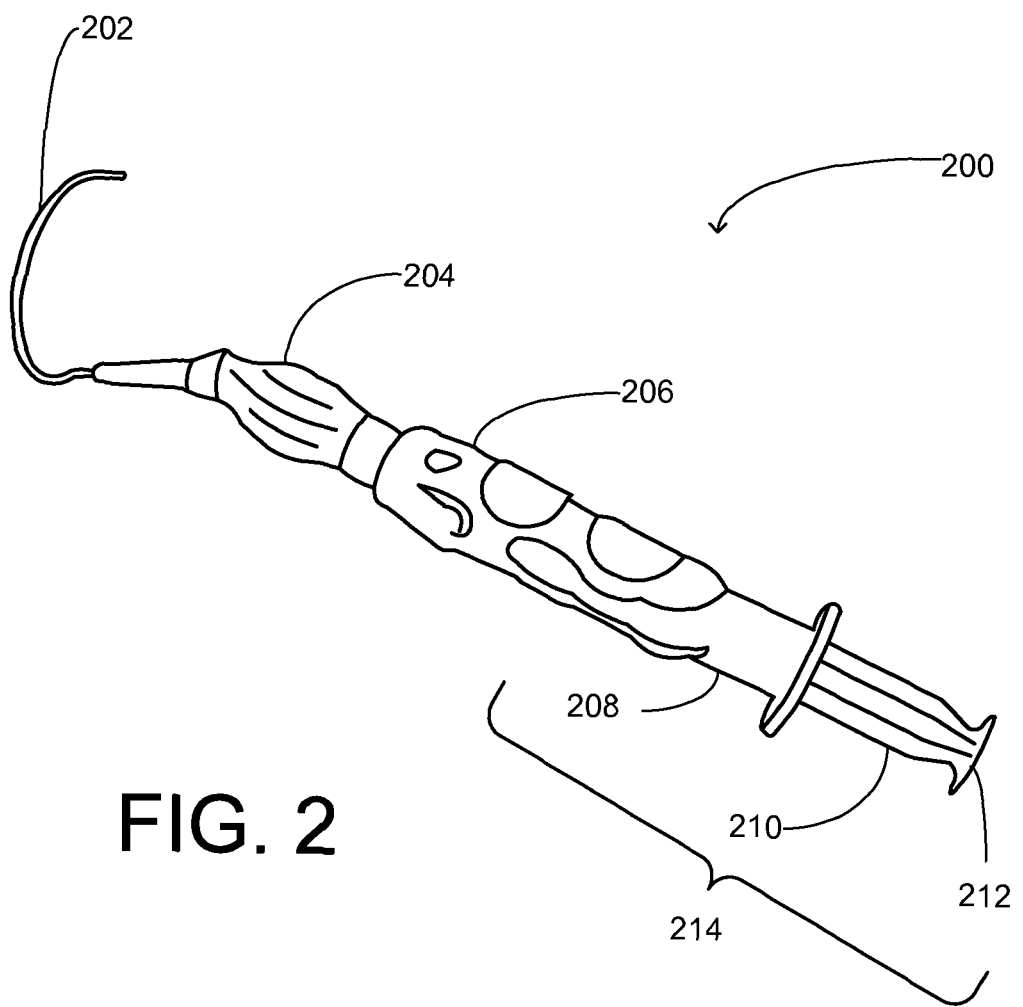
FIG. 2 is a perspective view of a delivery device according to an example embodiment.

FIG. 2 is a perspective view of a delivery device 200 according to an example embodiment. The delivery device 200 may include features or components similar to those included in the delivery device 100 described with reference to FIG. 1. In this example, the delivery device 200 may include a bulbous member 204, which may perform functions, and have features, similar to the pump 104 described with reference to FIG. 1. For example, in the illustrated embodiment, the bulbous member 204 includes a partial ellipsoid, with a major axis parallel to a longitudinal axis of the delivery device 200 and/or a portion of a needle 202 which resides inside the pump 204. The bulbous member 204 may have two ends, which may be compression-sealed or glued to a handle 206.

The bulbous member 204 may be made of a flexible material, such as plastic, which may be biased to the expanded configuration. When pressure is applied to the bulbous member 204, the bulbous member 204 may deform into the collapsed configuration with the smaller volume than the expanded configuration. When the bulbous member 204 is deformed into the collapsed configuration, the fluid stored in the bulbous member 204 may flow out of the bulbous member 204 via the needle 202. When pressure is released from the bulbous member 204, fluid from outside the delivery device 200, such as from the patient, may flow into the bulbous member 204 via the needle 202, but a one-way valve (not visible in FIG. 2) causes the fluid to not flow back to a reservoir (described below) of the delivery device 200.

The delivery device 200 may also include the handle 206. The handle 206, and the hook shape of the needle 202 in this example shown in FIG. 2, may facilitate a transobturator approach. In other words, the handle 206 and the shape of the needle 202 allow the physician to insert the delivery device 200 into a body of a patient and towards or through an obturator foramen of the patient. In other embodiments, the handle 206 and needle 202 are shaped to facilitate the placement of the delivery device 200 into a different portion of the body of the patient.

The handle 206 may be rigidly connected to, or integrally manufactured with, such as by injection molding, the bulbous member 204 and the needle 202. The rigid connection of the handle 206 to the bulbous member 204 may allow the user or practitioner of the delivery device 200 to control the needle 202 by holding and controlling the handle 206 and/or bulbous member 204.

Rather than integrally manufacturing the bulbous member 204 with the handle 206, the bulbous member 204 and handle 206 may be manufactured separately. The bulbous member 204 and handle 206 may be connected or coupled by friction fitting or by tabs or flanges and grooves, according to example embodiments.

The handle 206 may include rigid or irregular patterns to allow a human user to grip the delivery device 100. The handle 206 may also receive a reservoir 214, which may have features and/or functions similar to the reservoir 114 shown in and described with reference to FIG. 1. The handle 206 may removably receive the reservoir 214, allowing the reservoir 214 to be easily removed from the delivery device 200. The reservoir 214 may, for example, be secured into the handle 206 by friction fitting, and/or by the securement to the bulbous member 204 via the one-way valve.

The reservoir 214 may be a syringe, which may include a cylindrical barrel 208, which may be connected by friction fitting, or via a hub into (described below), or may be separate from, the handle 206, as shown in FIG. 2, and a plunger 210. The cylindrical barrel 208 may store fluid when sealed by the plunger 210. The plunger 210 may fit into and/or seal with the cylindrical barrel 208, such as by a rubber tip (which may be similar to the rubber tip shown in and described with reference to FIG. 5B). A user or practitioner of the delivery device 200 may apply pressure to a button 212 of the plunger 210, causing a tip or end (not shown in FIG. 2) of the plunger 210 to move toward a bottom of the cylindrical barrel 208, thereby forcing the fluid from the reservoir 214 into the bulbous member 204.

Figure 3A:
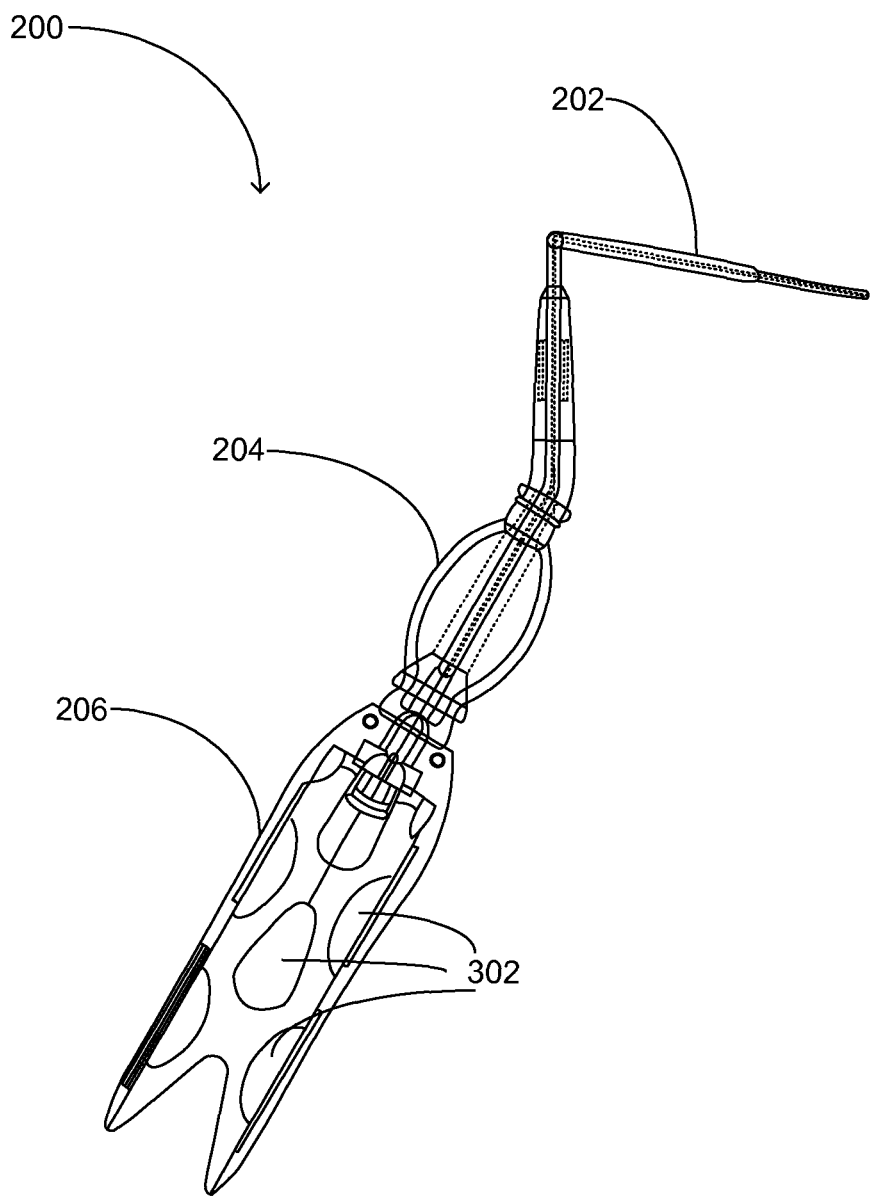
FIG. 3A is a side view of the delivery device shown in FIG. 2.

FIG. 3A is a side view of the delivery device 200 shown in FIG. 2. As shown in FIG. 3A, the handle 206 may be cylindrical, and may include apertures 302 which facilitate gripping the handle 206 and/or delivery device 200 by the user or practitioner.

Figure 3B:
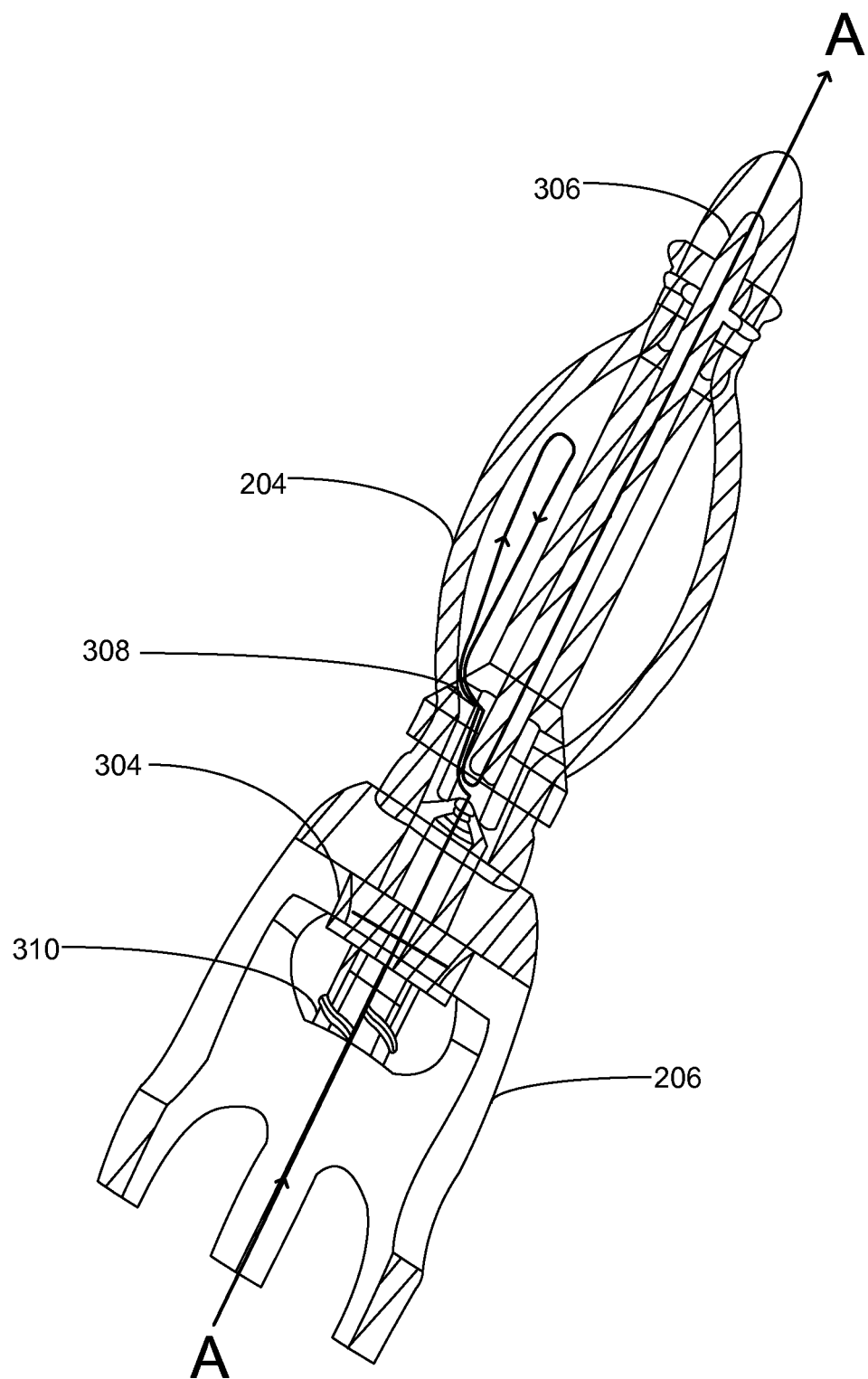
FIG. 3B is a cross-sectional view of a portion of the delivery device shown in FIG. 2.

FIG. 3B illustrates a portion of the delivery device 200 shown in FIG. 2. In this example, the fluid may flow from the reservoir 214 (not shown in FIG. 3B) through a one-way valve 304 (which may be similar in form and function to the one-way valve 112 described with reference to FIG. 1), into the bulbous member 204, through a needle shaft 306 of the needle 202 (shown in FIGS. 2 and 3A), and into the patient. The needle shaft 306 may be a portion of the needle 202 which extends into the bulbous member 204; the needle shaft 306 may be straight and/or cylindrical, and may extend into the bulbous member 204 along a center longitudinal axis, denoted 'A' in FIG. 3B, of the bulbous member 204 and/or delivery device 200. The arrow A shows the path of the fluid from the reservoir 214 to the patient through the one-way valve 304, bulbous member 204, needle shaft 306, and needle 202. Also, fluid from the patient, such as blood or urine, may flow along the path in an opposite direction, from the patient, through the needle shaft 306 of the needle 202, and into the bulbous member 204, but not through the one-way valve 304 or into the reservoir 214.

In the example shown in FIG. 3B, the bulbous member 204 may include a bulb inlet and outlet port 308. The bulb inlet and outlet port 308 may couple to the one-way valve 304, and may receive fluid from the reservoir 214 via the one-way valve 304.

FIG. 3B shows a configuration of the one-way valve 304 which includes a tabbed hub 310 configured to screw into a threaded cylinder on an outside of the barrel 208 of the reservoir 214. The tabs of the hub 310 may securely engage into the threads of the threaded cylinder, removably coupling the bulbous member 204 to the reservoir 214 (not shown in FIG. 3B). The tabbed hub 310 may include a luer hub configured to screw into the threaded cylinder of the reservoir 214.

Figure 3C:
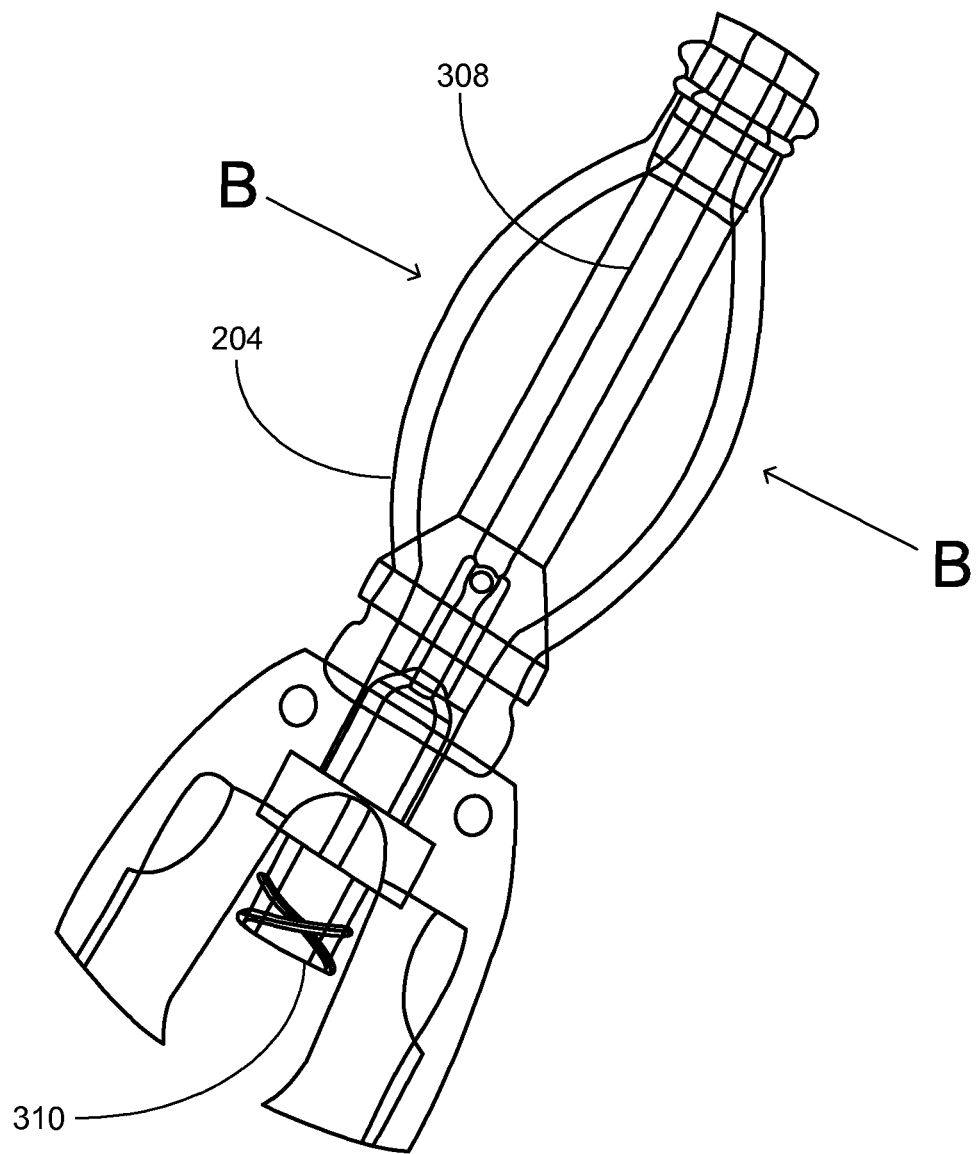
FIG. 3C illustrates a portion of the delivery device shown in FIG. 2.

FIG. 3C illustrates a portion of the delivery device shown in FIG. 2 according to an example embodiment. Arrows B show directions in which pressure may be applied to the bulbous member 204, deforming the bulbous member 204 into the collapsed configuration and causing the fluid to flow out of the bulbous member 204 and into the patient via the needle 202 (not shown in FIG. 3C). In this example, the bulb inlet and outlet port 308 has been moved forward to ease priming the bulbous member 204. A user of the delivery device 200 can prime the pump or bulbous member 204 by holding the delivery device 200 upright, with the needle 202 facing away from the ground, removing or purging air from the bulbous member 204.

The handle 206 may be coupled to the reservoir 214 by friction fitting the reservoir 214 into an aperture of the handle 206, or the reservoir 214 may be coupled to the handle 206 via a tether or tube, or the handle 206 may be separate from the reservoir 214. The coupling by friction fitting may allow a user or practitioner of the delivery device 200 to control the entire delivery device 200 with one hand, whereas the coupling by a tether or tube may allow the user to set the reservoir 214 on a table or other platform, reducing the weight of the portion of the delivery device 200 which must be held and controlled by the user or practitioner.

Figure 3D:
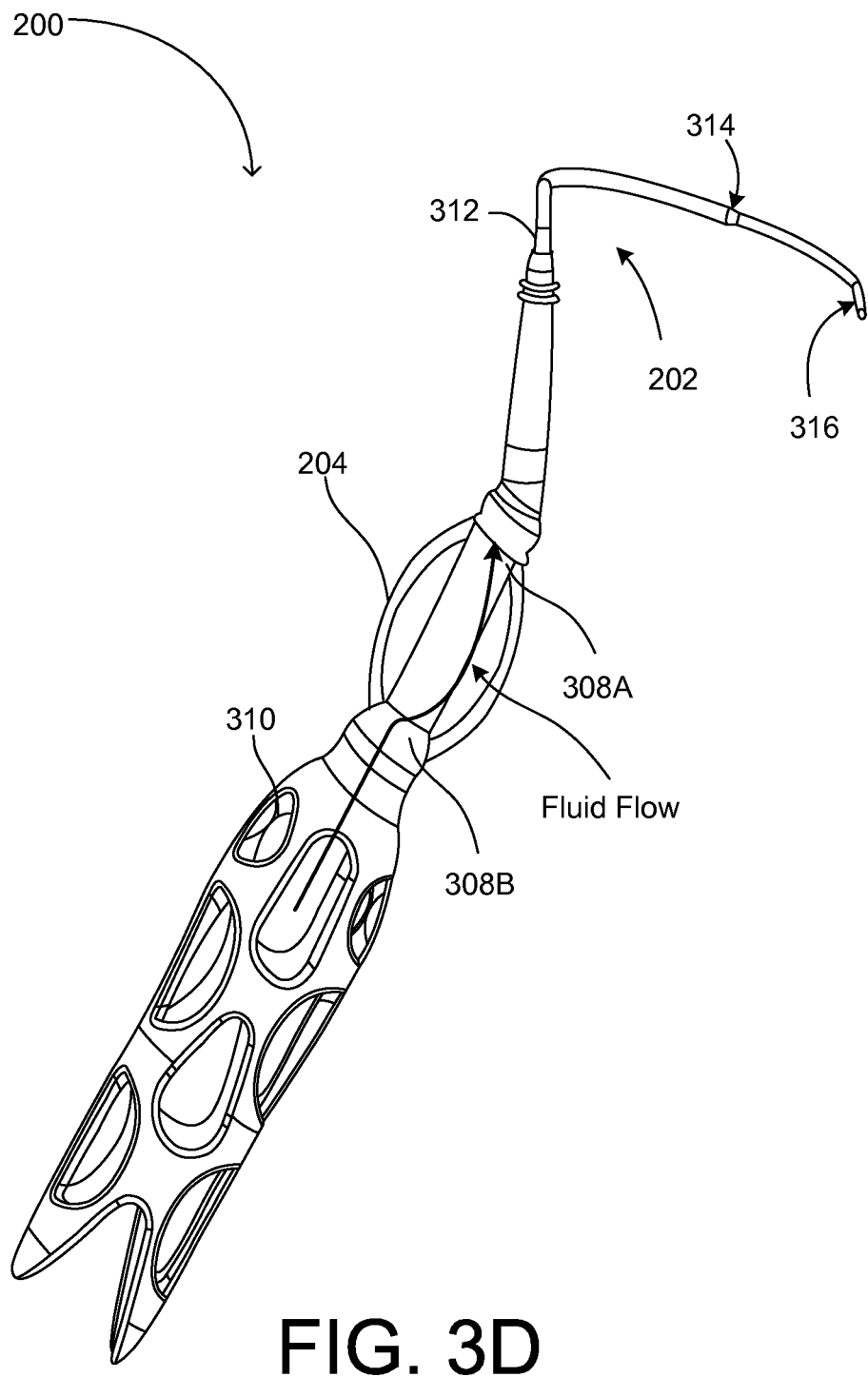
FIG. 3D is a perspective view of a delivery device according to another example embodiment.

FIG. 3D is a perspective view of a delivery device 200 according to another example embodiment. The delivery device 200 shown in FIG. 3D may include similar features to those described above with respect to FIGS. 2, 3A, 3B, and 3C. The needle 202 of the delivery device may be hook-shaped, and may include a second curve or bend, so that an end portion 316 of the needle 202 extends in a direction which is generally opposite (or nearly parallel to) a base portion 312 of the needle 202. The needle 202 may include three portions: a base portion 312 extending from the bulbous member 204, a middle portion 314 which extends generally perpendicularly from the base portion 312, and an end portion 316 which extends nearly perpendicularly from the middle portion 314, according to an example embodiment.

The bulbous member 204 may include a lumen port 308A coupled to the needle 202, which allows fluid to flow between the bulbous member 204 and the needle 202. The bulbous member 204 may also include a hub port 308B coupled to the hub 310, which allows fluid to flow from the hub 310 and reservoir 214 (not shown in FIG. 3D) to the bulbous member 204. Fluid may flow from the hub port 308B to the lumen port 308A along the path labeled, "Fluid Flow," facilitating priming of the pump or bulbous member 204 by removing air from the bulbous member 204, according to an example embodiment.

Figure 3E:
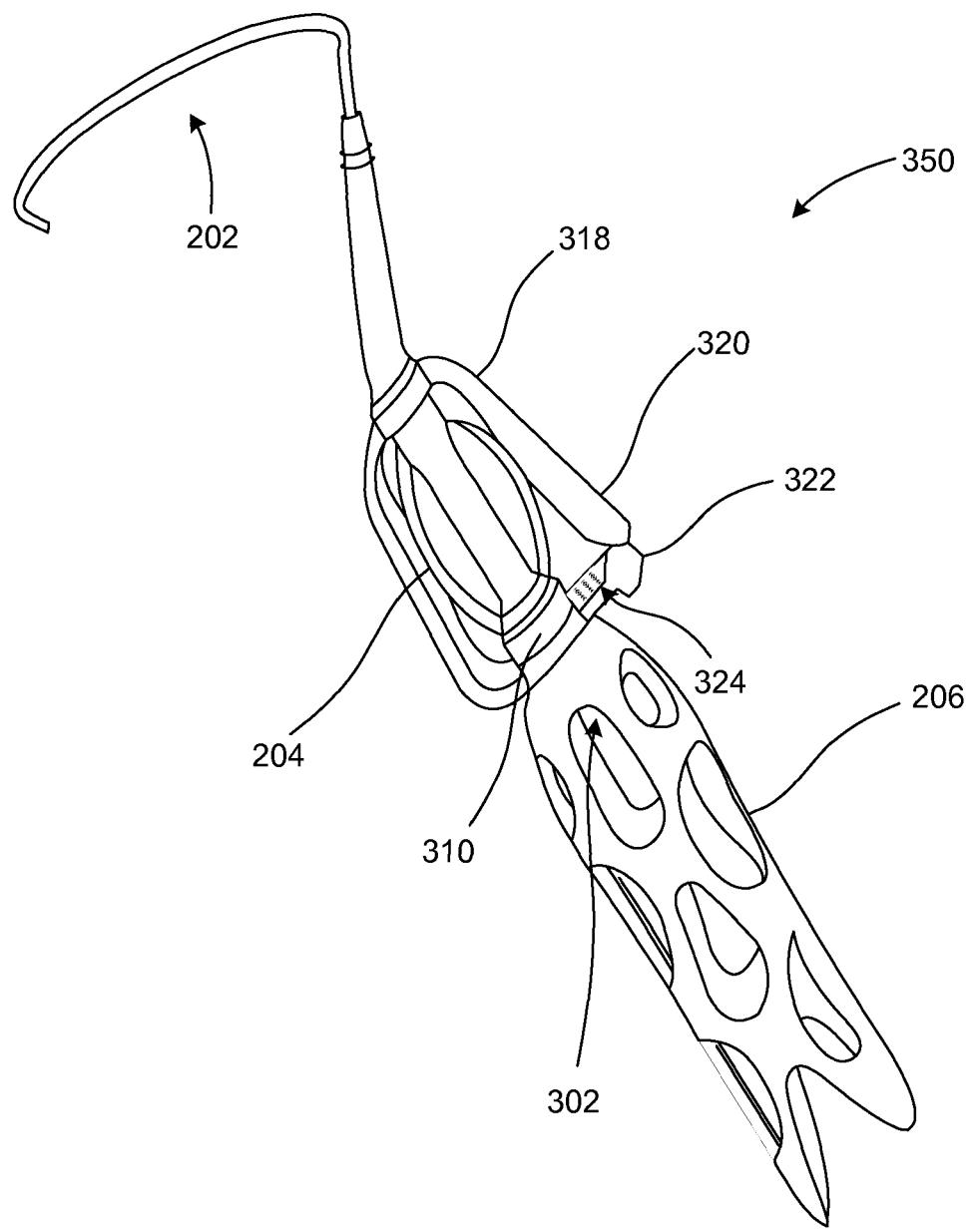
FIG. 3E is a perspective view of a delivery device according to another example embodiment.

FIG. 3E is a perspective view of a delivery device 350 according to another example embodiment. The delivery device 350 shown in FIG. 3E may include similar features to the delivery device 200 described above with respect to FIGS. 2, 3A, 3B, 3C, and 3D. The delivery device 350 shown in FIG. 3E may also include an aspiration or injection clip 318. The clip 318 may be coupled or secured to the needle 202. For example, the needle 202 may extend through an aperture of the clip 318, and the clip 318 may thereby be friction fitted to the needle 202.

The clip 318 may maintain the bulbous member 204 in a collapsed or partially collapsed configuration, ready for aspiration. The clip 318 may include a cantilever 320. The cantilever 320 may include a rigid member which is flexibly secured to the needle 202, such as by the friction fitting of the aperture of the clip 318 to the needle 202, and the flexibility of the portion of the clip 318 where the cantilever 320 extends from the clip 318. The flexible securement of the cantilever 320 to the needle 202 may be similar to a hinged attachment, allowing the cantilever to rotate against and away from the bulbous member 204, applying and releasing pressure to and from the bulbous member 204.

The clip 318 may also include a lever 322. The lever 322 may extend from the bulbous member and/or from the hub 310. The lever 322 may secure the position of the cantilever 320 against the bulbous member 204. The lever 322 may include teeth 324 which increase friction between the lever 322 and the cantilever 320, further securing the position of the cantilever 320 against the bulbous member 204. The teeth 324 may be spaced apart from each other in regular intervals, such as about one millimeter, or any other interval.

The spacing of the teeth 324 at regular intervals from each other may regulate injection of fluid from the bulbous member 204 through the needle 202 into the patient. For example, a user of the delivery device 350 may inject fluid into the patient by pushing the cantilever 320 with enough force to cause the cantilever 320 to press into the bulbous member 204 and slide along the lever 322 by one tooth 324; the cantilever 320 may advance from one tooth 324 on the lever 322 to an immediately succeeding or adjacent tooth 324. The regular spacing of the teeth 324 from each other may cause a same amount of fluid to be injected with each moving of the cantilever 320 to a successive tooth 324 of the lever 322, according to an example embodiment.

A user of the delivery device 350 may press the cantilever 320 against the bulbous member 204, forcing fluid out of the bulbous member 204, and the lever 322 and teeth 324 may prevent the cantilever 320 from retracting or expanding away from the bulbous member 204, preventing the bulbous member 204 from expanding and preventing fluid from re-entering the bulbous member 204. The teeth 324 can hold the lever 322 in a closed position, maintaining pressure against the bulbous member 204, preventing the bulbous member 204 from expanding without requiring the user to continue exerting pressure on the bulbous member 204. The user may then rely on the teeth 324 and lever 322 to hold the bulbous member 204 in a collapsed or partially collapsed state while the anesthetic in the fluid takes effect on the patient. The user may pull the lever 322 down, releasing the cantilever 320, allowing the cantilever to expand away from the bulbous member 204, and allowing the bulbous member 204 to expand and receive fluid, according to an example embodiment.

Figure 4:
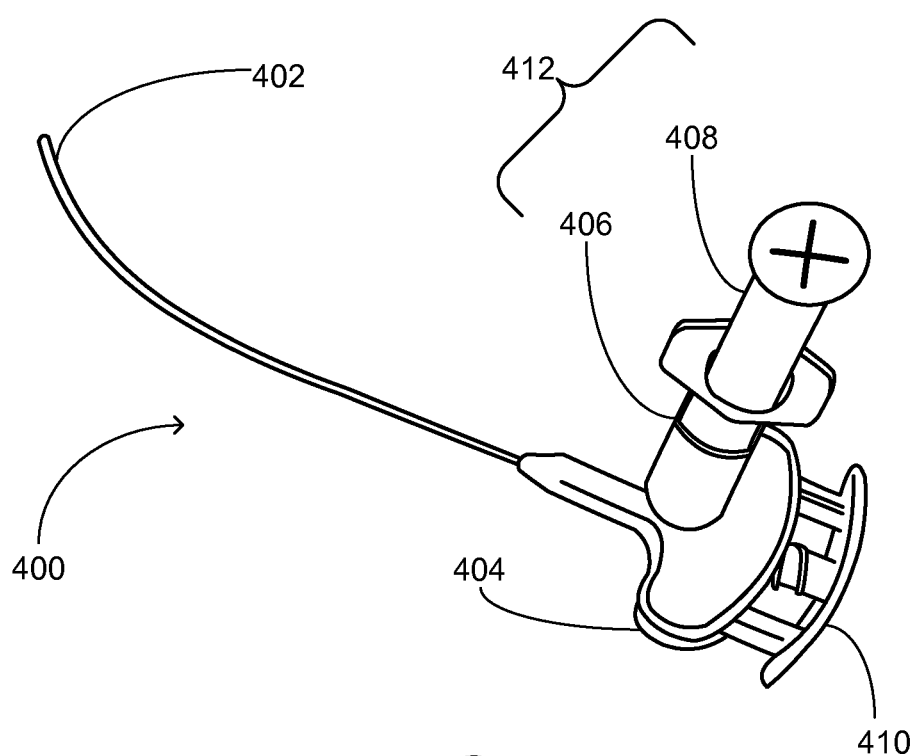
FIG. 4 is a perspective view of a delivery device according to another example embodiment.

FIG. 4 is a perspective view of a delivery device 400 according to another example embodiment. The delivery device 400 may include features or components similar to those included in the delivery device 100 described with reference to FIG. 1. The delivery device 400 may include a needle 402 and a handle 404; the curve of the needle 402 and the shape of the handle 402 and reservoir 412 (which may have features and perform functions similar to the reservoir 114 described with reference to FIG. 1, and may include a barrel 406 and plunger 408) may facilitate the delivery of an implant via a retro-pubic approach. In other words, the curve of the needle 402, in this embodiment, might facilitate the advancing of the delivery device through a skin incision and into a region, such as a pelvic region, of the patient.

In this example, the handle 404 may be wing-shaped, and may receive and/or be coupled to a palm button 410. The pump 502 (which performs functions similar to the pump 104 described with reference to FIG. 1, and which is shown in and further described with reference to FIG. 5A) may include the handle 404 and the palm button 410 in this example. In this example, a user or practitioner may use the palm of his or her hand to apply pressure to the palm button 410 to force the pump 502 into the collapsed configuration and cause fluid to exit the pump via the needle 402 into the patient. The pressure may be resisted by a spring, shown and described below.

Figure 5A:
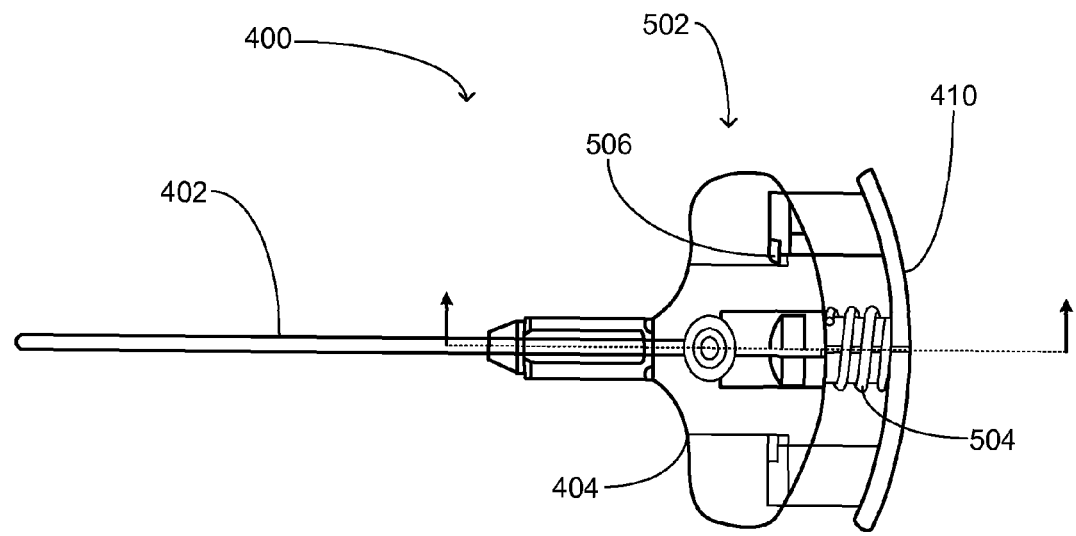
FIG. 5A is a top view of the delivery device shown in FIG. 4.

FIG. 5A is a top view see-through illustration of the delivery device 400 according to the example shown in FIG. 4. In this example, the pump 502 may include a spring 504 which forces the palm button 410 of the pump 504 away from the pump 502. The spring 504 may resist pressure on the palm button 410 applied by the user or practitioner of the delivery device 400 to place the pump 502 in the collapsed configuration. The spring 504 may bias the pump 502 into the expanded configuration by resisting the pressure on the palm button 410, and may force the palm button 410 away from a bottom of a cavity of the pump 502 (described below with reference to FIG. 5B), and cause the pump 502 to return to its expanded state when pressure is released from the palm button 410. The pump 502 may also include a latch 506. The latch 506 may limit movement of a plunger (described below with reference to FIG. 5B) and the palm button 410 away from an end of the pump 502 closer to the needle 402, thereby preventing the palm button 504 from falling away from the pump 502, and/or may prevent a plunger from exiting the cavity.

Figure 5B:
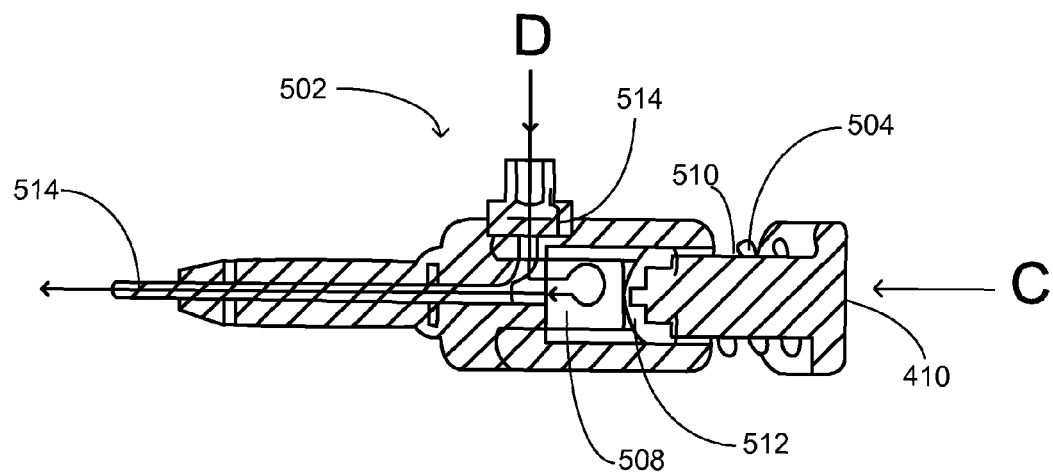
FIG. 5B is a cross-sectional view of the delivery device shown in FIG. 4.

FIG. 5B is a cross-sectional view of the delivery device 400 according to the example shown in FIG. 4. In this example, the pump 502 may include a cavity 508. The cavity 508 may include an aperture or barrel which stores the fluid inside the pump 502. The cavity 508 may, for example, be cylindrical.

The cavity 508 may receive a plunger shaft 510. The plunger shaft 510 may, when traveling toward the bottom of the cavity 508 in the direction denoted by arrow C, cause the medicinal fluid to be expelled from the pump 502 into the patient via the needle 402. A plunger tip 512 may be in contact with the fluid, and may form a seal with the cavity 508, preventing the fluid from exiting the cavity 508 and/or the pump 502. The plunger tip 512 may be made of rubber or other compressible material to facilitate sealing with the cavity 508. The spring 504 may force the pump 502 into the expanded state by forcing the plunger shaft 510 away from the bottom of the cavity 508.

When the pump 502 receives fluid from the reservoir 412 (not shown in FIG. 5B) and delivers the fluid to the patient via the needle 402, the fluid may flow along the path denoted by arrow D. The fluid may flow through a one-way valve 514 (which may have similar features and perform similar functions to the one-way valve 112 described with reference to FIG. 1), into the cavity 508 of the pump 502, through the needle 402 and its needle shaft 514, and into the patient. When the pump 502 receives fluid from the patient, such as when pressure is released from the button 410, the fluid may flow from the patient through the needle 402 and its needle shaft 514 into the cavity 508 of the pump 502, but not through the one-way valve 514.

When coupled or connected to the pump 502, a longitudinal axis of the reservoir 412 may be orthogonal or perpendicular to the needle shaft 514. Additionally, in the illustrated embodiment, the longitudinal axis of the reservoir 412 is orthogonal or perpendicular to a longitudinal axis of the handle 404. This orthogonal arrangement may allow the needle 402 and/or needle shaft 514 to be injected into the patient in a direction parallel to the ground or floor, while the reservoir 412 extends in an upward direction, away from the ground or floor, allowing gravity to force the fluid from the reservoir 412 into the pump 502.

Figure 5C:
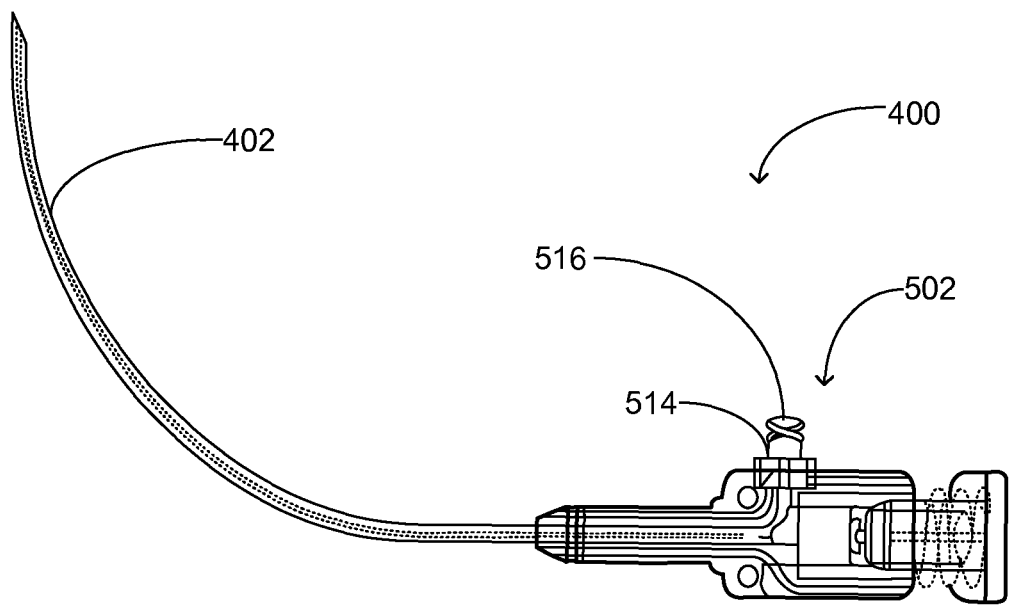
FIG. 5C is a side view of the delivery device shown in FIG. 4.

FIG. 5C is a side view of the delivery device 100 according to the example shown in FIG. 4. This figure shows the one-way valve 514 extending away from the pump 502. In this example, the one-way valve 514 may be perpendicular to a length of the cavity 508 (not shown in FIG. 5C) and/or the needle shaft 514 (not shown in FIG. 5C). The reservoir 412 (not shown in FIG. 5C) may be removably coupled to the pump 502 via the tabbed hub of the one-way valve 514. FIG. 5C also shows the curve of the needle 402, which may facilitate the needle 402 bypassing organs of a patient to reach areas which could not be reached with a straight needle without penetrating the organs.

Figure 5D:
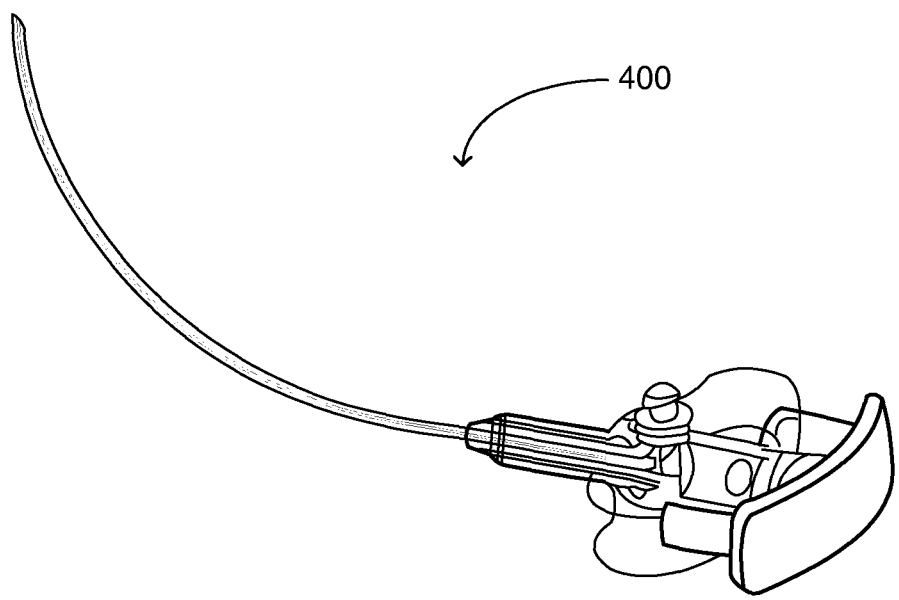
FIG. 5D is a perspective view of the delivery device according to the example shown in FIG. 4.

FIG. 5D is a perspective view of the delivery device 400 according to the example shown in FIG. 4.

Figure 6:
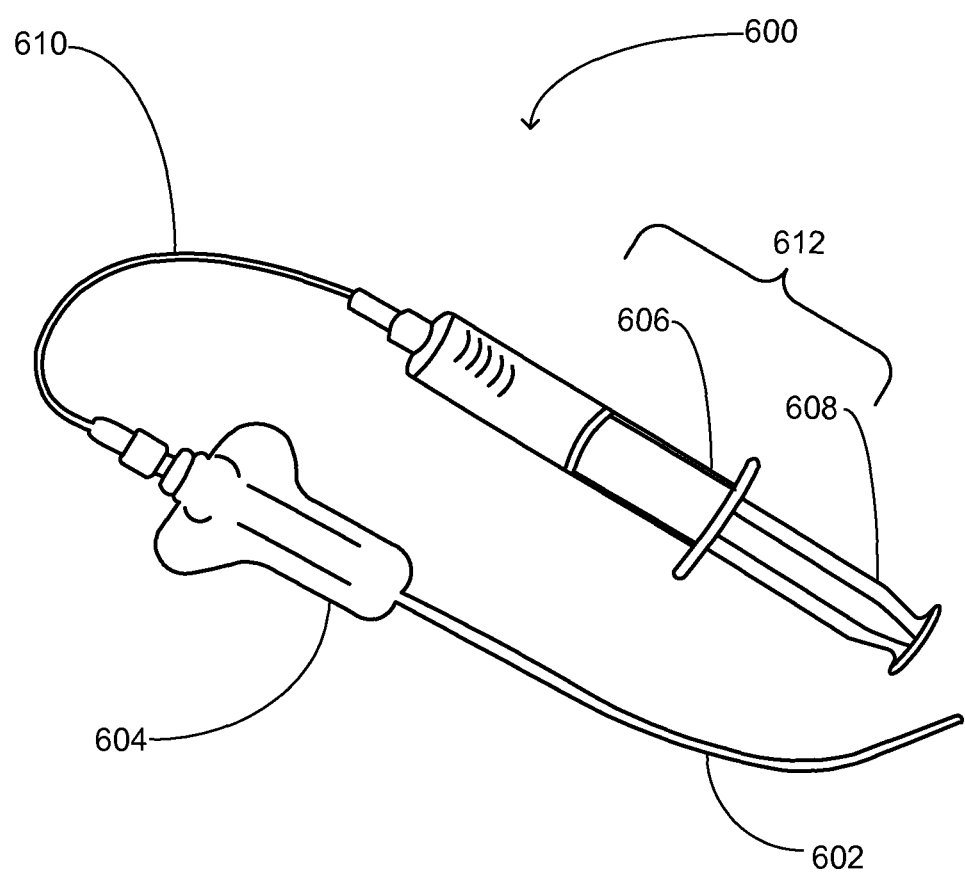
FIG. 6 is a perspective view of a delivery device according to another example embodiment.

FIG. 6 is a drawing of the delivery device 600 according to another example embodiment. The delivery device 600 may include features or components similar to those included in the delivery device 100 described with reference to FIG. 1. The curve of the needle 602 and the integral manufacturing of the handle with the pump 604 may facilitate a supra-pubic approach. In this example, the pump 604 may be coupled to a reservoir 612 (which may include features and perform functions similar to the reservoir 114 described with reference to FIG. 1 and include a barrel 606 and a plunger 608) via a tube 610. The tube 610 may be flexible, and allow the reservoir 612 to be disposed a distance from the pump 604. The tube 610 may allow the reservoir 612 to be placed in various locations while a user of the delivery device 600 utilizes the pump 604 and the needle 602. The disposal of the reservoir 612 a distance from the pump 604 may allow the user or practitioner of the delivery device 600 to control the needle 602 and pump 604 without the reservoir 612 and fluid stored in the reservoir adding to the weight held by the user or practitioner.

The pump 604 may be made of a flexible material, such as plastic, which may be biased to an expanded configuration. When pressure is applied to the pump 604, the pump 604 may deform into a collapsed configuration with a smaller volume than the expanded configuration. When the pump 604 is deformed into the collapsed configuration, the fluid stored in the pump 604 may flow out of the pump 604 via the needle 602. When pressure is released from the pump 604, fluid from outside the delivery device 600, such as from the patient, may flow into the pump 604 via the needle 602, but a one-way valve (not visible in FIG. 6) causes the fluid not to go back to the reservoir 114, which includes the barrel 606 and the plunger 608.

Figure 7:
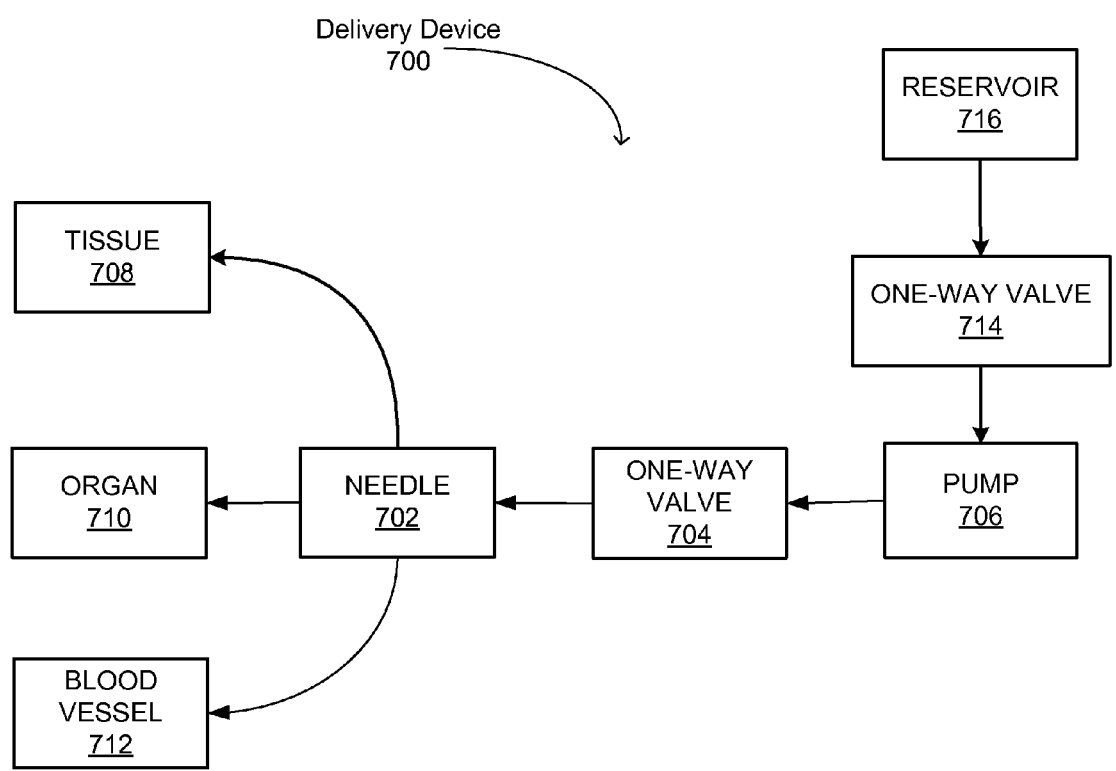
FIG. 7 is a block diagram of a delivery device according to another example embodiment.

FIG. 7 is a block diagram of a delivery device 700 according to another example embodiment. In this example, the delivery device 700 includes a needle 702, a pump 706, a one-way valve 714, and a reservoir 716 which have features and perform functions with respect to a patient's tissue(s) 708, organ(s) 710, and/or blood vessel(s) 712 which are similar to those described with reference to FIG. 1 regarding the needle 102, pump 104, tissue 106, organ 108, blood vessel 110, one-way valve 112, and reservoir 114. The reservoir 716 may be removably coupled to the pump 706 and/or one-way valve 714, such as by friction fitting or by tabs and grooves. However, in this example, the delivery device 700 includes a one-way valve 704 coupled between the needle 702 and the pump 706. The one-way valve 704 may prevent fluids from flowing from the needle 702 into the pump 706. The one-way valve 704 may have a cracking pressure similar to, or different from, the cracking pressure of the one-way valve 112 and/or the one-way valve 714. In some embodiments, the one-way valve 704 operatively coupled between the needle 702 and the pump 706 prevents the aspiration by the device 700 but facilitates the priming of the pump 706.

Figure 8:
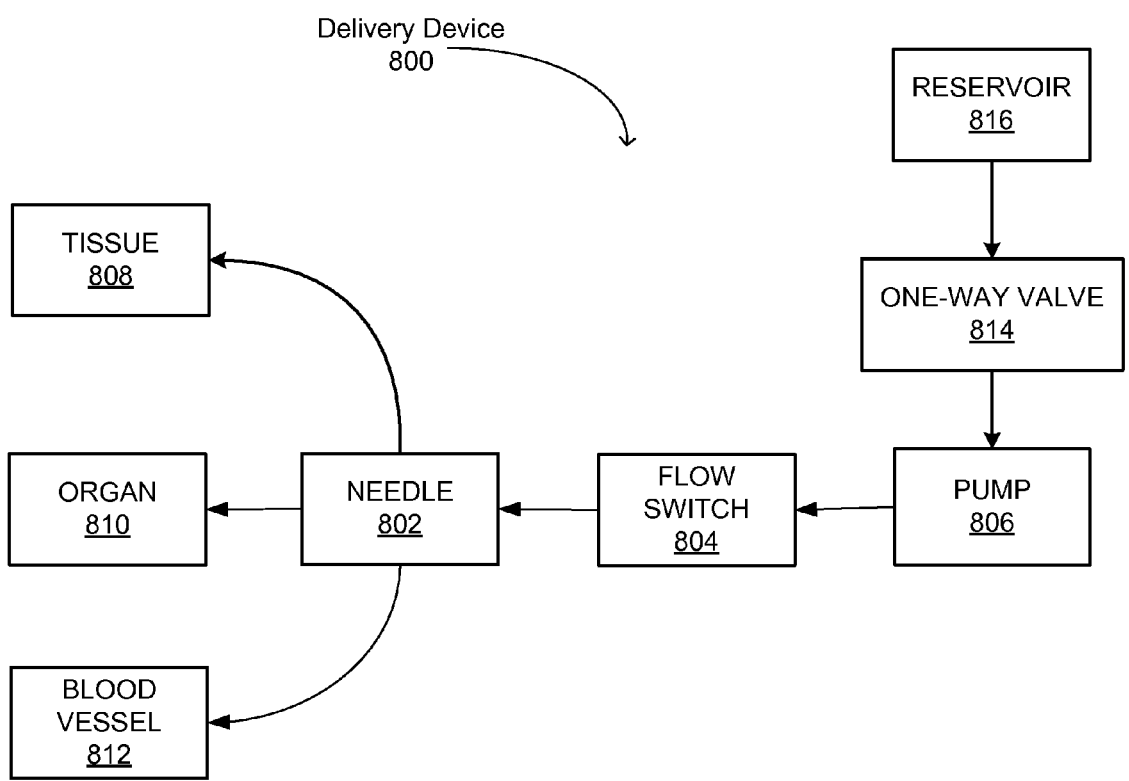
FIG. 8 is a block diagram of a delivery device according to another example embodiment.

FIG. 8 is a block diagram of a delivery device 800 according to another example embodiment. In this example, the delivery device 800 includes a needle 802, a pump 806, a one-way valve 814, and a reservoir 816 which have features and perform functions with respect to a patient's tissue(s) 808, organ(s) 810, and/or blood vessel(s) 812 which are similar to those described with reference to FIG. 1 regarding the needle 102, pump 104, tissue 106, organ 108, blood vessel 110, one-way valve 112, and reservoir 114. The reservoir 816 may be removably coupled to the pump 806 and/or one-way valve 814, such as by friction fitting or by tabs and grooves. However, in this example, the delivery device 800 includes a flow switch 804 coupled between the needle 802 and the pump 806. The flow switch 804 may be turned on (or opened), allowing fluid to flow between the needle 802 and the pump 806, and may be turned off (or closed), preventing fluids from flowing between the needle 802 and the pump 806. A user or practitioner may, for example, pressurize the pump 806 with the flow switch turned off with a measured volume, so that when the when the flow switch 804 is turned on, the measured volume will be expelled as the pump 806 is returned to atmospheric pressure. The user or practitioner may elect not to inject the entire measured amount of fluid by turning the flow switch 804 to off before all of the fluid has been expelled.

Figure 9:
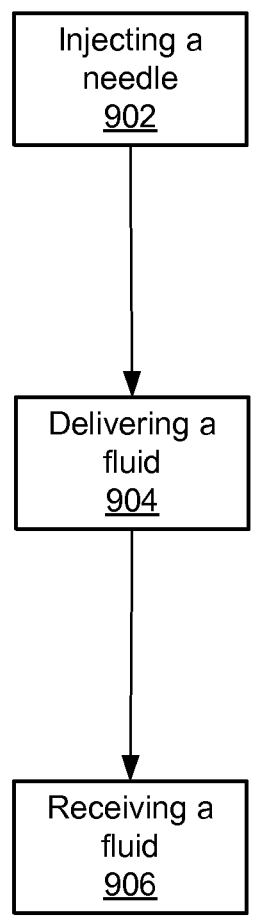
FIG. 9 is a flowchart showing a method according to an example embodiment.

FIG. 9 is a flowchart showing a method 900 according to an example embodiment. In this example, the method 900 may include injecting a needle of a delivery device into a patient (902). The method 900 may also include delivering a medicinal fluid from the delivery device into the patient by applying pressure to a pump of the delivery device (904). Applying pressure to the pump may cause the pump to collapse into a smaller configuration, forcing the fluid out of the pump into the patient. The method 900 may also include receiving a bodily fluid from the patient into the delivery device by releasing the pressure from the pump (906). The user or practitioner of the delivery device may, for example, release the pressure from the pump to allow the pump to expand to its original expanded configuration and cause the bodily fluid to aspirate from the patient into the pump.

In an example embodiment, the method 900 may further include viewing the received bodily fluid in the delivery device. The user or practitioner may, for example, view the bodily fluid through a transparent material of the pump. The method 900 may further include determining a location of the needle based on a color of the received bodily fluid. For example, if the bodily fluid is yellow, the needle may be in a urethra or bladder of the patient, and if the bodily fluid is red, the needle may be in a blood vessel of the patient. The practitioner may change the course or location of the needle based on the determined location.

In an example embodiment, the method 900 may also include delivering additional medicinal fluid from the delivery device into the patient by advancing a plunger into a barrel of a reservoir of the delivery device. The practitioner may, for example, press the plunger into the barrel to inject fluid from the reservoir into the patient, or to force fluid from the pump 104 into the patient.

In an example embodiment, the method 900 may include pouring or disposing the medicinal fluid into the delivery device. For example, the practitioner may pour the fluid into the barrel of the reservoir, seal the barrel with the plunger, and prime the delivery device by pressing the plunger into the barrel until all the air is released from the delivery device.

In some embodiments, a delivery device includes a needle and a pump. The pump is operatively coupled to the needle. The pump has an expanded configuration and a collapsed configuration. The pump is biased to its expanded configuration such that fluid stored in the pump will exit the pump via the needle in response to pressure being applied to the pump, and in response to the pressure being released from the pump, the pump is configured to receive fluid from outside of the delivery device via the needle.

In some embodiments, the needle is curved. In some embodiments, the pump includes a transparent material that makes a color of the fluid stored in the pump visible to a user of the delivery device. In some embodiments, the pump includes a bulbous member made of a flexible material biased to the expanded configuration such that the bulbous member deforms into the collapsed configuration with a smaller volume than the expanded configuration in response to the pressure being applied to the pump, causing the fluid stored in the pump to exit the bulbous member via the needle. The bulbous member returns to the expanded configuration in response to the pressure being released from the pump, causing the fluid outside the delivery device to enter the bulbous member via the needle.

In some embodiments, the pump includes a cavity configured to store fluid stored in the pump and to receive a plunger. The plunger is disposed within the cavity. The plunger is configured to cause the fluid stored in the pump to exit the pump via the needle by collapsing the pump into the collapsed configuration when the plunger moves toward a bottom of the cavity, and to return the pump to its expanded configuration when the plunger moves away from the bottom of the cavity, causing the fluid outside the delivery device to enter the pump via the needle. In some embodiments, a spring is coupled to both the cavity and the plunger. The spring is configured to bias the pump to the expanded state by resisting pressure forcing the plunger toward the bottom of the cavity and, when the pressure forcing the plunger toward the bottom of the cavity is released, to force the plunger to move away from the bottom of the cavity.

In some embodiments, the pump includes a latch configured to prevent the plunger from exiting the cavity. In some embodiments, the one-way valve includes a tabbed hub configured to screw into a threaded cylinder of a reservoir. In some embodiments, the one-way valve includes a luer hub configured to screw into a threaded cylinder of a reservoir.

In some embodiments, the device includes a one-way valve coupled to the pump. The one-way valve is configured to couple to a reservoir. The valve is also configured to allow the pump to receive fluid from the reservoir via the one-way valve. The valve is also configured to prevent fluid from flowing from the pump to the reservoir via the one-way valve.

In some embodiments the deliver device includes a reservoir coupled to the one-way valve, the reservoir being configured to store fluid, and a reservoir plunger configured to force the fluid from the reservoir into the pump via the one-way valve when the reservoir plunger moves toward a bottom of the reservoir. In some embodiments, the reservoir is cylindrical. In some embodiments, the reservoir is removably coupled to the delivery device or pump.

In some embodiments, the device includes a handle rigidly connected to the one-way valve and the pump. The rigid connection maintains a fixed arrangement between the handle, the one-way valve, and the pump. The handle includes a cylindrical aperture configured to receive the reservoir. In some embodiments, the reservoir is disposed a distance from the pump. In some embodiments, a flexible tube couples the one-way valve to the reservoir.

In some embodiments, a delivery device includes a needle and a pump operatively coupled to the needle. The pump is configured to store medicinal fluid for injection into a patient via the needle. In some embodiments, a reservoir is removably coupled to the pump. The reservoir is configured to store and provide the medicinal fluid to the pump.

In some embodiments, the reservoir is removably coupled to the pump via a one-way valve. The one-way valve is configured to allow the medicinal fluid to flow from the reservoir into the pump and prevent the medicinal fluid from flowing from the pump into the reservoir. In some embodiments, the reservoir includes a cylindrical barrel and a reservoir plunger configured to force the medicinal fluid from the reservoir into the pump when the reservoir plunger moves toward a bottom of the cylindrical barrel.

In some embodiments, a method includes (1) injecting a needle of a delivery device into a patient; (2) delivering a medicinal fluid from the delivery device into the patient by applying pressure to a pump of the delivery device; and (3) receiving a bodily fluid from the patient into the delivery device by releasing the pressure from the pump.

In some embodiments, the method includes viewing the received bodily fluid in the delivery device, and determining a location of the needle based on a color of the received bodily fluid. In some embodiments, the method includes delivering additional medicinal fluid from the delivery device into the patient by advancing a plunger into a reservoir of the delivery device. In some embodiments, the method includes disposing the medicinal fluid into the delivery device.

While certain features of the described implementations have been illustrated as described herein, many modifications, substitutions, changes and equivalents will now occur to those skilled in the art. It is, therefore, to be understood that the appended claims are intended to cover all such modifications and changes as fall within the true spirit of the embodiments of the invention.

What is claimed is:

1. A delivery device comprising:
a needle including a needle shaft defining a lumen;
a pump operatively coupled to the needle, the pump including a bulbous member, the bulbous member configured to store fluid, the lumen of the needle shaft being in fluid communication with the bulbous member, the pump having an expanded configuration and a collapsed configuration, the bulbous member including a flexible material, the flexible material biasing the pump to the expanded configuration, the fluid stored in the bulbous member configured to exit the bulbous member of the pump via the needle in response to a user applying pressure to the pump, and in response to the pressure being released from the pump, the pump is configured to return to the expanded configuration causing fluid from outside of the delivery device to enter the bulbous member via the needle;
a handle coupled to the bulbous member, the bulbous member being disposed between the handle and the needle, the handle including a valve; and
a reservoir removably coupled to the handle, the valve permitting a transfer of fluid from the reservoir to the bulbous member in a first direction.

2. The delivery device of claim 1, wherein the needle is curved.

3. The delivery device of claim 1, wherein the flexible material of the bulbous member includes a transparent material that makes a color of the fluid stored in the pump visible to the user of the delivery device.

4. The delivery device of claim 1, wherein the reservoir includes a threaded portion, and the valve includes a tabbed hub, the tabbed hub configured to screw into the threaded portion of the reservoir.

5. The delivery device of claim 1, wherein the reservoir includes a threaded cylinder, and the valve includes a one-way valve, wherein the one-way valve includes a luer hub configured to screw into the threaded cylinder of the reservoir.

6. The delivery device of claim 1, wherein the valve prevents a transfer of the fluid from the bulbous member to the reservoir in a second direction.

7. The delivery device of claim 1, further comprising a reservoir plunger configured to force the fluid from the reservoir into the bulbous member via the valve when the reservoir plunger moves toward a bottom of the reservoir.

8. The delivery device of claim 1, wherein the reservoir is cylindrical.

9. The delivery device of claim 1, wherein the handle defines a plurality of apertures.

10. The delivery device of claim 1, further comprising an injection clip configured to be coupled to the needle, the injection clip defining an aperture, the needle configured to extend through the aperture of the injection clip, the injection clip including a movable portion configured to apply and release pressure to and from the bulbous member.

11. The delivery device of claim 1, wherein the reservoir is disposed a distance from the pump.

12. The delivery device of claim 1, further comprising a flexible tube coupling the valve to the reservoir.

13. The delivery device of claim 1, wherein the needle shaft of the needle includes a needle portion extending into the bulbous member.

14. A delivery device comprising:
a needle including a needle shaft defining a lumen;
a handle having a longitudinal axis, the handle including a valve;

a reservoir removably coupled to the handle, and a bulbous expandable member having a distal end portion and a proximal end portion, the distal end portion of the bulbous expandable member being coupled to the needle, the proximal end portion of the bulbous expandable member being coupled to the handle, the bulbous expandable member including a partial ellipsoid having a major axis parallel to the longitudinal axis of the handle, the bulbous expandable member configured to store fluid, the bulbous expandable member being disposed between the handle and the needle, the valve permitting a transfer of the fluid from the reservoir to the bulbous member but preventing a transfer of the fluid from the bulbous member to the reservoir, the bulbous expandable member having an expanded configuration and a collapsed configuration, the bulbous expandable member including a flexible material, the flexible material biasing the bulbous expandable member to the expanded configuration, the fluid stored in the bulbous expandable member configured to exit the bulbous expandable member via the needle in a first direction in response to a user applying pressure to the bulbous expandable member, and in response to the pressure being released from the bulbous expandable member, the bulbous expandable member is configured to return to the expanded configuration causing bodily fluid to enter the bulbous expandable member via the needle in a second direction, the second direction being opposite to the first direction.

15. The delivery device of claim 14, wherein the handle defines a cavity having a shape configured to receive the reservoir.

16. The delivery device of claim 14, wherein the reservoir is a syringe defining a cylindrical barrel.

17. The delivery device of claim 14, wherein the flexible material of the bulbous expandable member includes a transparent flexible material that makes a color of the bodily fluid stored in the bulbous expandable member visible to the user of the delivery device.

18. The delivery device of claim 14, wherein the needle includes a curved needle portion extending from the bulbous expandable member, and a linear portion extending into the bulbous expandable member.

\* \* \* \* \*